US005720303A

United States Patent [19]

Richardson

[11] Patent Number: 5,720,303

[45] Date of Patent: Feb. 24, 1998

[54] PORTABLE STRETCHER SYSTEM

[76] Inventor: Patrick J. Richardson, 6901 Wimbledon Ct., New Market, Md. 21774

[21] Appl. No.: 780,612

[22] Filed: Jan. 8, 1997

[51] Int. Cl.[6] .......... A61F 5/37

[52] U.S. Cl. .......... 128/870; 5/625; 5/627

[58] Field of Search .......... 128/845, 846, 128/869, 870, 873, 874, 876; 5/600, 624, 625, 628

[56] References Cited

U.S. PATENT DOCUMENTS

| | | | |
|---|---|---|---|
| 2,489,828 | 11/1949 | Springer | 5/625 |
| 3,336,060 | 8/1967 | Bradford | 403/108 |
| 4,628,945 | 12/1986 | Johnson | 602/27 |
| 4,679,260 | 7/1987 | Fretten | 5/627 |
| 4,979,520 | 12/1990 | Boone | 128/876 |
| 5,421,273 | 6/1995 | Lin | 108/187 |

*Primary Examiner*—Michael A. Brown
*Attorney, Agent, or Firm*—Morton J. Rosenberg; David I. Klein; Jun Y. Lee

[57] ABSTRACT

A flexible stretcher (100) and a tubular carrying case (170) are included in a stretcher system (10). Flexible stretcher (100) is formed by a pliant body member (102) having a head support portion (104), a torso support portion (110) and a leg support portion (106). The torso support portion includes a stiffened section (112) disposed between a pair of flexible side sections (114, 116). The stiffened section (112) includes three pockets (118, 122 and 126), each pocket having a respective stiffening member (120, 124 and 128) disposed therein. The three pockets (118, 122 and 126) are provided with a detachable closure (155) through which any of the slats (120, 124 and 128) may be replaced. Detachable closure (155) is formed by a pair of complementary hook-and-loop type fastening elements (158 and 160).

4 Claims, 5 Drawing Sheets

PORTABLE STRETCHER SYSTEM

BACKGROUND OF THE INVENTION

1. Field of the Invention

This invention directs itself to stretcher systems for use in transporting injured personnel. More in particular, this invention directs itself to a portable stretcher system having a flexible stretcher and carrying case for receipt of the flexible stretcher therein. More in particular, this invention directs itself to a portable stretcher system wherein the flexible stretcher is formed by a pliant body member having a torso support portion with both a stiffened section and a pair of flexible side sections. Further, this invention directs itself to a stiffened section of a flexible stretcher having three pockets disposed in laterally spaced relationship, each pocket being closed on one longitudinal end thereof and open on an opposing end. Within each of the pockets is disposed a stiffening member which may be removed through the open end of the pocket. Still further, this invention directs itself to a stiffened section of a flexible stretcher wherein the open end of each of the plurality of pockets is provided with a detachable closure to provide retention and selective replacement of stiffening members disposed within the plurality of pockets.

2. Prior Art

Stretchers are well known in the art. The best prior art known to the Applicant include U.S. Pat. Nos. #722,456; #2,272,681; #2,350,573; #2,489,828; #3,158,875; #4,492,225; and, #5,121,756.

Some prior art systems, such as that disclosed in U.S. Pat. Nos. #722,456; #2,272,681; and, #2,350,573 are directed to stretcher systems having stiffening portions disposed between respective head and foot portions. Such systems disclose the use of wooden slats for adding support to the stretcher body and where such slats may be disposed within pockets. However, where pockets are disclosed, such are not provided with any type of detachable closure to permit replacement of the wooden slats.

Prior art stretchers, such as Reeves Model No. 101 and Reeves Model No. 105, manufactured by REEVES MANUFACTURING COMPANY of Frederick, Md., are portable stretchers formed of a vinyl coated nylon sheet material having wooden slats securely sewn between two layers of the vinyl coated material. Here again, such prior art stretchers do not provide for any means to replace the wooden stiffening slats when such become warped or damaged. Such systems further do not provide for a tubular carrying case into which the stretcher may be disposed to provide protection from being soiled or damaged during storage and transport to the site of its utilization.

SUMMARY OF THE INVENTION

A portable stretcher system is provided. The portable stretcher system includes a pliant body member extending both longitudinally and laterally. The pliant body member has a head supporting portion on one longitudinal end thereof, a portion for supporting a patient's legs disposed on an opposing longitudinal end, and a torso supporting portion disposed intermediate the head supporting portion and the leg supporting portion. The torso supporting portion has (1) a stiffened section defined by three longitudinally extended pockets formed in laterally spaced relationship, each of the pockets being closed on one longitudinal end thereof and open on an opposing end, and (2) a pair of flexible side sections disposed respectively on opposing lateral sides of the stiffened section. The head supporting portion and leg supporting portion each are adapted to be longitudinally foldable to overlay the torso supporting portion. The portable stretcher system also includes three support members that are removably received within the three pockets of the stiffened section. The portable stretcher system also includes a plurality of pairs of handle members affixed to the pliant body member. A respective pair of the plurality of pairs of handle members are affixed to the head supporting portion, torso supporting portion and leg supporting portion, respectively.

It is therefore an object of the invention to provide a stretcher system which is lightweight and sufficiently flexible to be tightly wrapped for storage in a carrying case.

It is another object of the invention to provide a stretcher system having a stiffened section of predetermined dimensions to adequately support the body of an injured person being transported on the stretcher, yet sufficiently limited in size to permit the stretcher to be folded into a small tubular cylindrical form for storage.

It is a further object of the invention to provide a stiffened section defined by three pockets, each pocket having one closed end and one open end for receipt of a stiffening member therein.

It is a still further object of the invention to provide replaceable stiffening members.

It is yet a further object of the invention to provide a releasable closure for the open ends of the stiffening member receiving pockets to retain the stiffening members and facilitate their replacement.

It is still another object of the invention to provide a carrying case for the stretcher having an open end with a releasable closure.

These and other advantages and novel features of the invention will become apparent from the following detailed description when considered in connection with the accompanying drawings wherein:

DESCRIPTION OF THE PREFERRED EMBODIMENT

Referring to FIGS. 1–5, there is shown, portable stretcher system 10 for providing a flexible stretcher 100 in a compact easy to transport package. As will be seen in following paragraphs, portable stretcher system 10 is specifically directed to a patient transport which is sufficiently flexible to partially wrap about the patient 14 for providing immobilization thereof, as well as being sufficiently flexible to be tightly wrapped and enclosed in a relatively small, lightweight carrying case, allowing the flexible stretcher 100 to be easily transported to the patient's location. Where an accident occurs in remote locations with limited access and/or rugged terrain, such as may be found in conjunction with an airplane crash or mountain climbing accident, it is important for the rescue personnel to be able to easily transport their rescue equipment to the location of the injured person. Thus, it is very important that such rescue devices as stretchers be formed of lightweight materials and of compact size. Yet, the reduced weight and compact size cannot be at the expense of the equipment's functionality. For instance, a stretcher must be capable of immobilizing the injured person while providing a means to transport that person without causing any further injury. The materials used must also permit easy cleaning and disinfection to provide for subsequent reuse.

Figure 1:
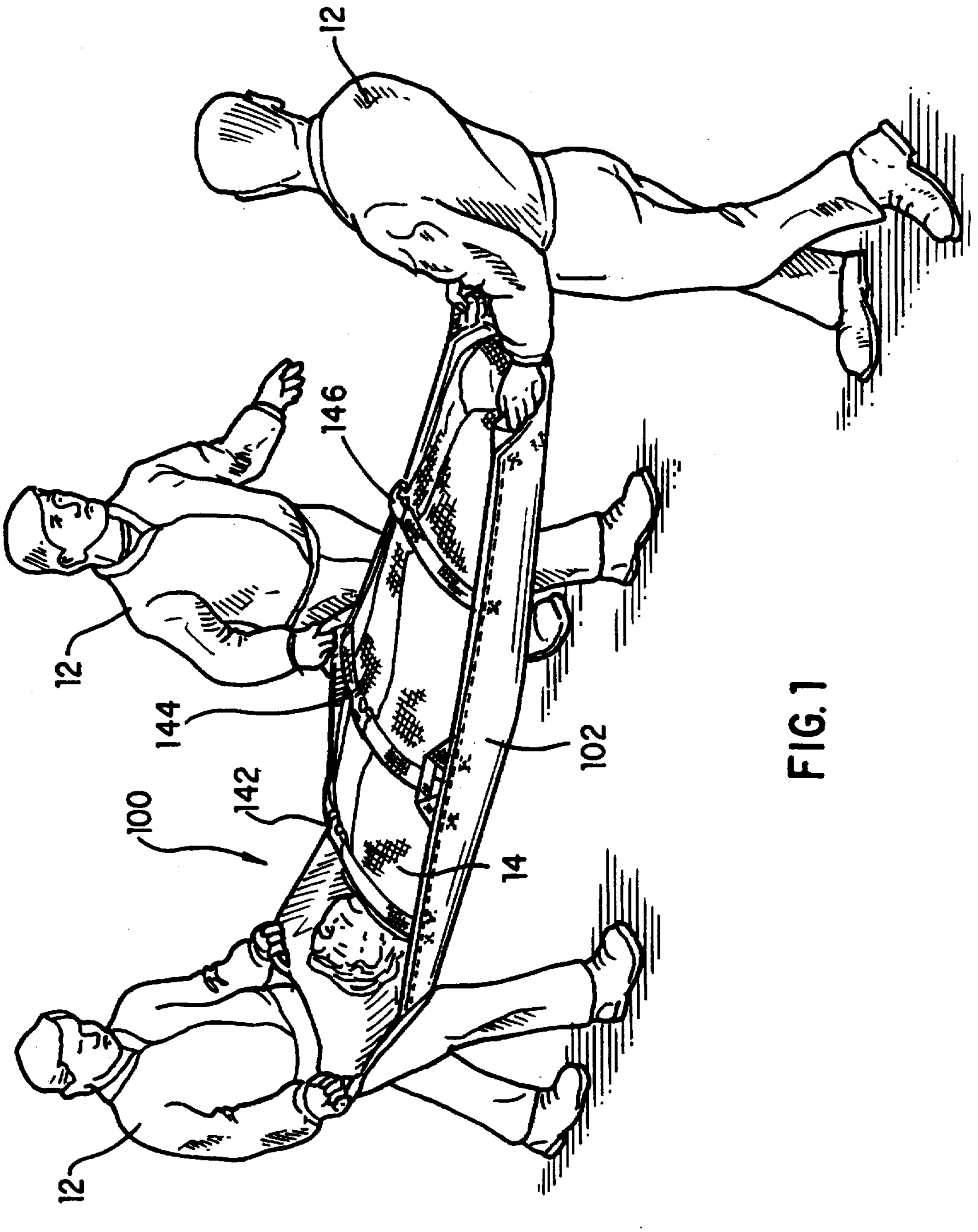
FIG. 1 is a perspective view depicting the use of the present invention.

Once deployed, the flexible stretcher 100, as shown in FIG. 1, must have sufficient structure to adequately support and immobilize the injured party 14 for transport from the accident site by the rescue personnel 12. By virtue of its flexibility, stretcher 100 immobilizes the patient placed thereon. The patient 14 is immobilized by means of a plurality of restraint straps 142, 144, 146, which extend laterally between opposing longitudinal sides of stretcher 110. The restraint straps 142, 144, and 146, when tightened, pull the longitudinal perimeter portion of the pliant body member 102 about the patient to provide further immobillzation thereof, by cradling the patient within the stretcher 100. However, the portion of stretcher 100 underlying the patient's spine should not be flexible in a longitudinal direction.

Figure 2:
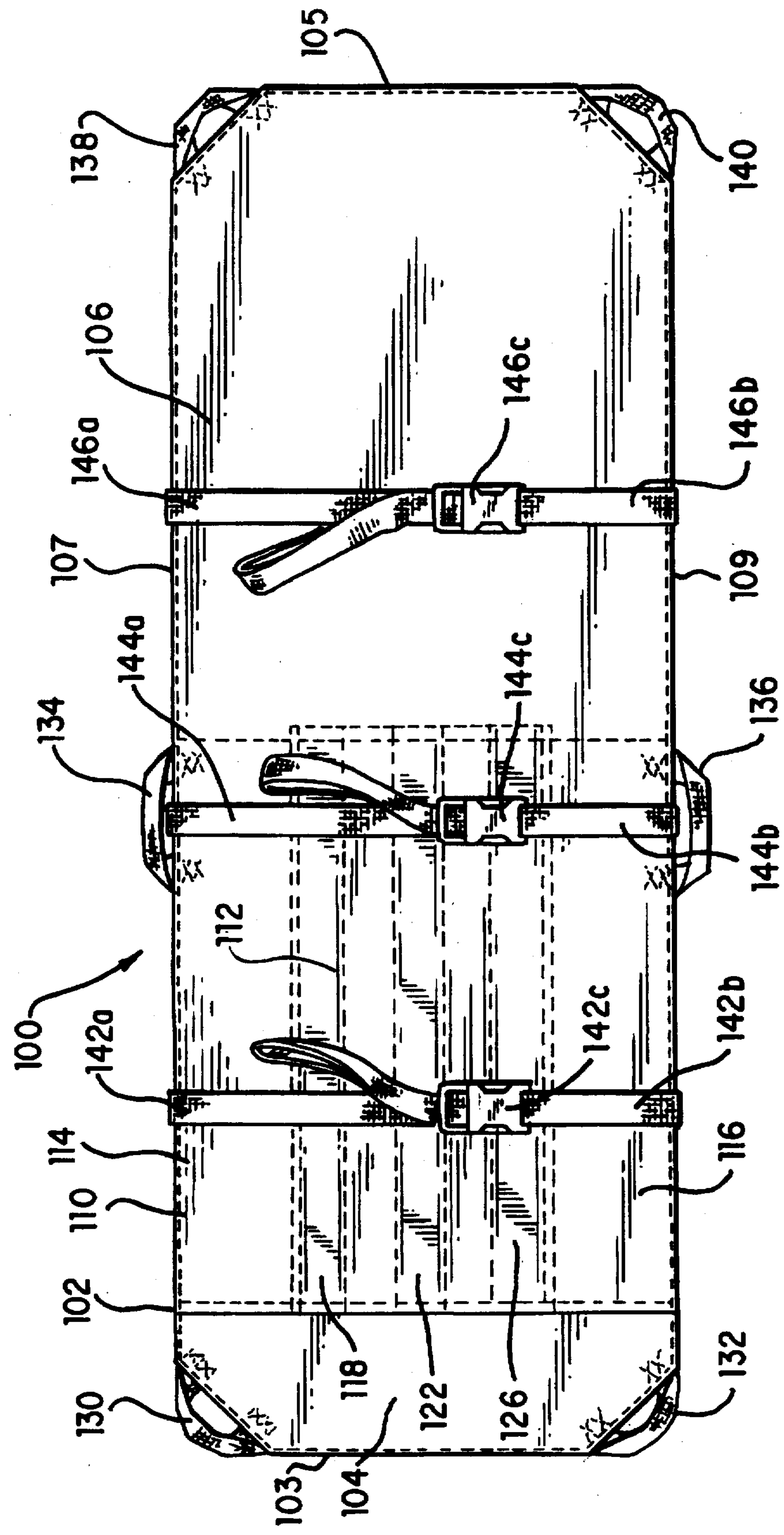
FIG. 2 is a plan view of the present invention.
Figure 3:
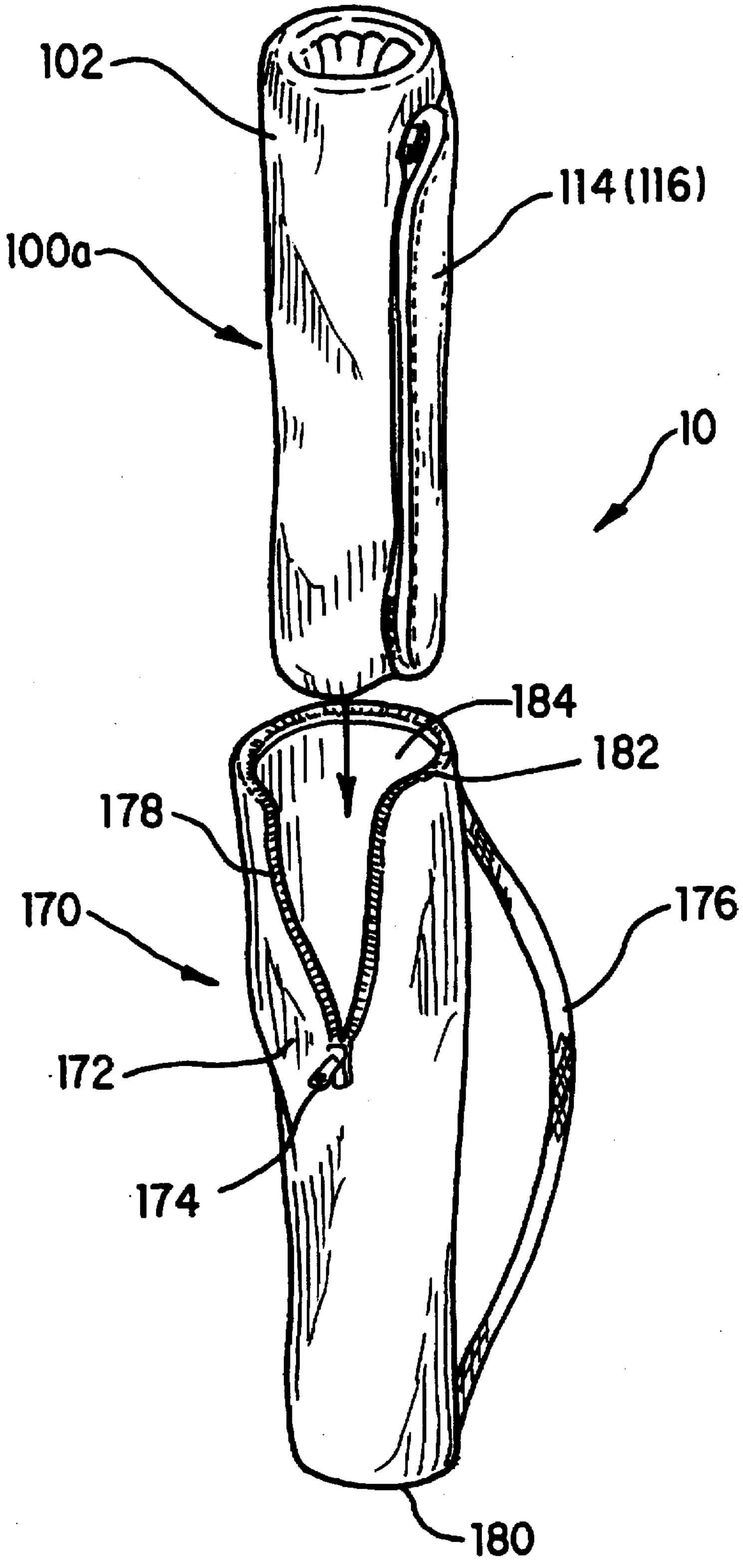
FIG. 3 is a perspective view showing the stretcher of the present invention wrapped for storage and the carrying case of the present invention.

Referring now to FIG. 2, there is shown, the flexible stretcher 100 formed by a pliant body member 102 which extends longitudinally from an end 103 at a head support portion 104 to an opposing end 105 at the distal end of a leg support portion 106, and laterally between opposing longitudinal sides 107, 109 thereof. Disposed between the head portion 104 and the leg portion 106 there is provided a torso supporting portion 110. The torso supporting portion includes a stiffened section centrally disposed between a pair of flexible side sections 114, 116. As will be further described in following paragraphs, the stiffened section 112 includes three laterally spaced pockets 118, 122 and 126 having stiffening members disposed therein to provide a rigid support region underlying a patient's spine. As both the head and leg supporting portions 104, 106 are devoid of rigidizing structures, they are easily folded over the torso supporting portion when stretcher 100 is to be stored. The folded structure can then be rolled laterally to form a compact cylindrical form 100*a*, as shown in FIG. 3, for enclosure within the carrying case 170.

As shown in FIG. 2, flexible stretcher 100 is provided with a plurality of handle members 130, 132, 134, 136, 138 and 140. One pair of handle members 130, 132 being affixed to opposing sides of the head supporting portion 104 adjacent the end 103. Handle members 134, 136 are disposed on opposing sides of the torso support portion 110, and another pair of handle members 138, 140 are affixed to opposing sides of the leg support portion 106, adjacent the distal end 105 of pliant body 102. A patient may be restrained on stretcher 100 by means of a plurality of pairs of strap members 142*a*, 142*b*; 144*a*, 144*b*; and, 146*a*, 146*b*. Each of the respective pairs of straps are coupled to opposing longitudinal sides of stretcher 100. The free ends of the strap members 142*a* and 142*b* are releasably coupled one to the other by means of a buckle 142*c*, and the free end of each of the straps 144*a* and 144*b* is releasably coupled one to the other by means of the buckle 144*c*. Similarly, the free ends of each of the strap members 146*a* and 146*b* are releasably coupled, one to the other, by means of the buckle 146*c*.

Figure 4:
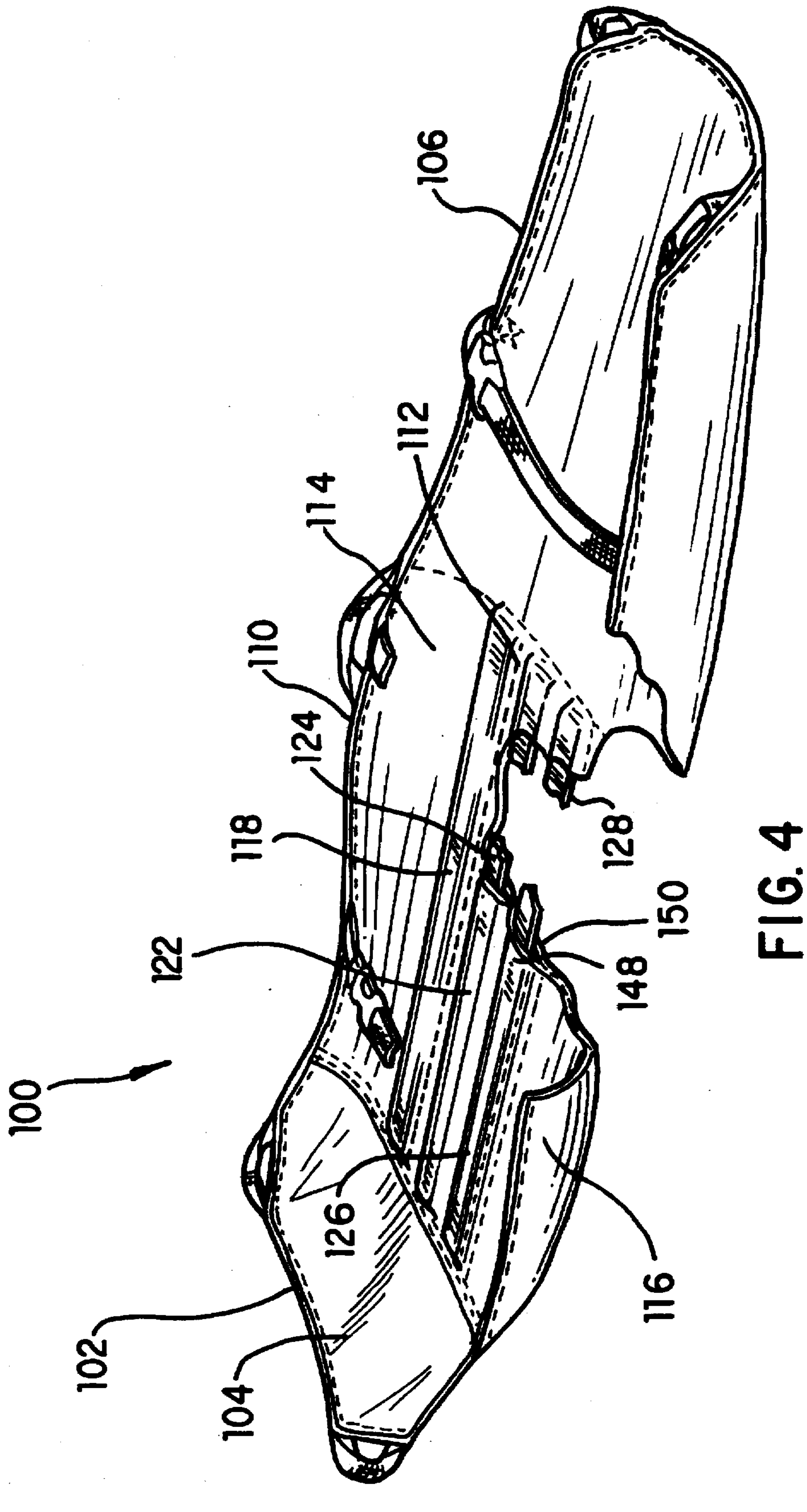
FIG. 4 is a perspective view, partially cut away, of the stretcher of the present invention; and, FIG. 5 is a sectional view of the present invention showing the detachable closure for the stiffening section thereof.

Referring additionally to FIG. 4, it can be seen that the torso support portion 110 of stretcher 100 is formed of multiple layers of material. A bottom layer 150 is defined by the structure of the pliant body member 102. The pliant body member 102 may be formed of a single layer of material or of a multi-layer structure, which single or multi-layer sheet material extends between opposing longitudinal ends 103, 105 of stretcher 100. An upper layer 148 overlays the torso support portion 110 and may also be formed by a single or multilayer sheet material. The sheets of material 148, 150 may each be formed by one or more layers of a plastic material composition or plastic composite material, such as plastic coated natural fibers or plastic coated synthetic fibers, such as a vinyl coated nylon. Utilization of a plastic or plastic coated material provides for easy cleaning of stretcher 100, resistance to penetration of liquids and resistance to deterioration by corrosive compounds. Use of plastic or plastic coated materials also permits stretcher 100 to be formed in bright colors, which is particularly important in certain applications, such as where law enforcement agencies are involved, such agencies require that their stretchers be colored in a bright or fluorescent orange color, to provide for easy identification.

Figure 5:
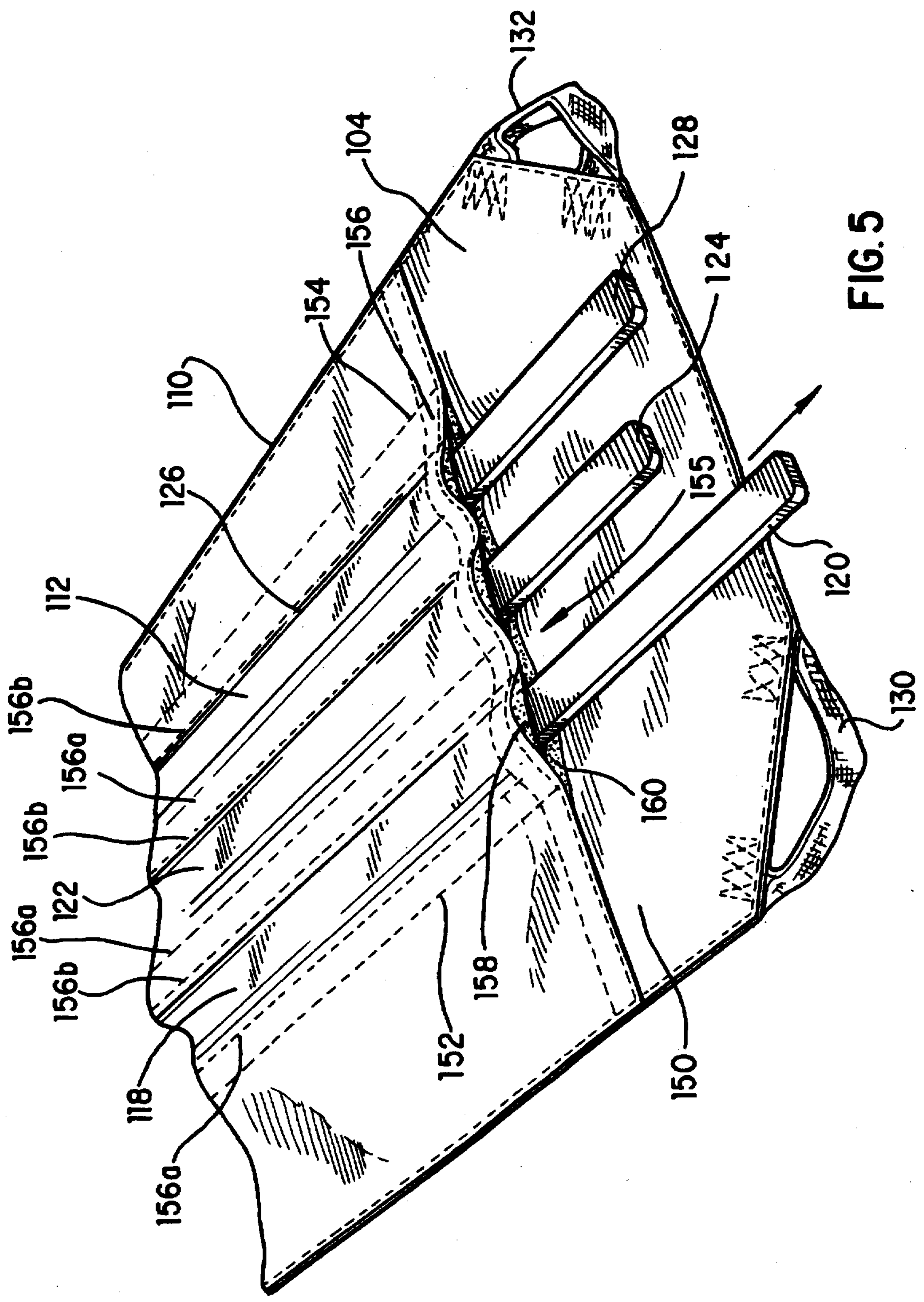

The stiffened section 112 is provided with three pockets defined by a gap between the layers 148 and 150 maintained between respective stitched seams 156*a* and 156*b*, shown in FIG. 5. Within each of the pockets 118, 122, and 126 there is provided a respective stiffening member 120, 124, and 128 extending continuously through substantially the entire torso supporting portion 110. Each of the stiffening members 120, 124, and 128 may be formed by a wooden slat or other material having sufficient rigidity to provide the necessary support of a patient's spinal region. Such other materials may include metallic materials, plastics, reinforced plastics and composites. As will be discussed in following paragraphs, stretcher 100 provides for replaceability of stiffening members 120, 124 and 128, thus stiffening members of different materials can be selectively installed or removed to accommodate a specific application. One application may require added buoyancy, while another could require greater stiffness than wooden slats provide. In particularly rugged terrain, where there is no danger of spinal injury, the stiffening members may be removed to make transport of the injured person easier. In an emergency situation, one or more of the stiffening members may be removed for use in forming a splint, without causing the destruction of stretcher 100.

By utilization of three support members, a centrally disposed support member 124 provides support directly below the expected location of the patient's spine, while the remaining two support members 120 and 128 are spaced laterally therefrom to insure that the patient's spinal region is well supported by a substantially rigid portion of the stretcher 100. Each of the stiffening members 120, 124 and 128 have an approximate width ranging from 2" to 3" and a longitudinal dimension within the range of 33" to 36", with the three members being laterally displaced one from another to define a stiffened section 112 having a lateral dimension of approximately 12" to 16" and a longitudinal dimension within the approximating range of 35" to 38". Each of the flexible side sections 114, 116 may thus extend 6" to 8" laterally from opposing sides of the stiffened section 112. The head support section 104 may extend longitudinally from the torso support section 110 approximately 9" to 10", while the leg support portion 106 extends longitudinally from the torso support portion 110 approximately 30" to 32".

Conventional, portable stretchers lose their usefulness when their stiffening members become warped or broken.

Since the conventional stretcher systems employ stiffening members which are sewn into the body of the stretcher, when such members fail, such requires replacement of the entire stretcher. As shown in FIG. 5, the pockets 118, 122 and 126 are provided with a disengageable closure whereby each of the slats 120, 124 and 128 can be withdrawn from the respective pocket 118, 122, 126 and replaced. Thus, if a slat becomes warped or broken, it may be easily removed from its location within a pocket and a new slat positioned therein. The disengageable or releasable closure is formed by an upper flap 156 that extends between longitudinal stitching 152 and 154, the stitching 152, 154 being disposed laterally from the respective endmost pockets 118, 126. The upper flap 156 extends across the opening of each of the three pockets 118, 122 and 126 and is provided with a fastening element 158 on an underside thereof. A complementary fastening element 160 is formed on an upper surface of the lower sheet material 150 in correspondence with the fastening element 158. The fastening elements 158 and 160 are defined by hook-and-loop type fastening elements, such as available under the trademark VELCRO. Hook-and-loop type fastening elements are particularly advantageous in this application, as such provide a seal across the entire lateral expanse of the stiffened section 112, and provides a great resistance to infiltration of fluids into the respective pocket regions. Further, hook-and-loop type fastening elements are not subject to inadvertent decoupling as the pliant body member 102 is flexed when it is removed from the carrying case 170 and unwrapped, as well as when it is wrapped and returned to the carrying case 170.

The stretcher 100 may be easily wrapped to form a compact cylindrical form 100*a* for storage within the carrying case 170. In forming the structure 100*a*, the head support portion 104 is folded longitudinally to overlie a portion of the torso support portion 110. Similarly, the leg support portion 106 is longitudinally folded to overlie a portion of the torso support portion 110. Lastly, the folded structure is rolled laterally, with one of the flexible side sections 114, 116 being disposed on an interior portion of the roll, and the respective other flexible side portion being on the exterior thereof. The wrapped cylindrical form 100*a* may then be enclosed within the carrying case 170.

Carrying case 170 may be formed of the same plastic or plastic coated material as that utilized for pliant body member 102, in either single or multiple plies. The carrying case 170 is formed by a tubular wall 172 having a closed bottom end 180. A shoulder strap 176 may be fastened to tubular wall 172 at opposing longitudinal ends thereof to provide for easy transport of system 10. Tubular wall 172 is formed with a slotted opening 178 extending longitudinally from the open end 182. Slotted opening 178 permits the opening at the upper end 182 to be enlarged as the rolled stretcher is passed into the cavity 184 defined by tubular wall 172. The perimeter of the open upper end 182 and the slotted opening 178 is provided with a zipper closure 174, maintaining the stretcher free of dirt and debris during storage and transport to a location where it is to be utilized. Although a zipper has been successfully used in one working embodiment, other types of closures may also be utilized.

Thus, it can be seen that portable stretcher system 10 is particularly advantageous to emergency rescue personnel where the size and weight of rescue equipment has a direct impact on the response time of such personnel. In particular, by limiting both the longitudinal and lateral dimensions of the stiffened section 110, such permits stretcher 100 to be wrapped into a very compact cylindrical form 100*a*, which is lightweight and easily transportable. Such compact form is further facilitated by limiting the number of stiffening members to three, which benefits both size and weight reduction of flexible stretcher 100. Utilization of an impervious plastic or plastic coated sheet material from which the pliant body member 102 is formed provides a flexible structure which is easily folded and wrapped to provide a compact form 100*a* for storage, and one which is able to cradle the patient being transported on stretcher 100, yet has the strength and durability of less flexible stretchers.

Particularly advantageous to rescue personnel, is the releasable closure 155 provided for the pockets 118, 122 and 126. By means of releasable closure 155, any of the slats 120, 124 and 128 may be removed from its respective pocket and replaced by another. In this manner, the warping or breakage of any one slat does not mean that the entire stretcher 100 must be replaced, making utilization of stretcher 100 highly efficient for emergency service organizations. Lastly, the provision of carrying case 170 as part of the portable stretcher system 10 further enhances advantages thereof. In addition to providing a convenient means for transporting stretcher 100, the carrying case 170 protects stretcher 100 from both dirt and damage during storage and handling by emergency service personnel.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is being claimed is:

1. A portable stretcher system comprising:

a pliant body member extending both longitudinally and laterally, said pliant body member having a head supporting portion on one longitudinal end thereof, a portion for supporting a patient's legs disposed on an opposing longitudinal end, and a torso supporting portion disposed intermediate said head supporting portion and said leg supporting portion, said torso supporting portion having (1) a stiffened section defined by not more than three longitudinally extended pockets formed in laterally spaced relationship, each of said pockets being closed on one longitudinal end thereof and open on an opposing end, and (2) a pair of flexible side sections disposed respectively on opposing lateral sides of said stiffened section, said head supporting portion and said leg supporting portion each being adapted to be longitudinally foldable to overlay said torso supporting portion said head supporting portion and said leg supporting portion each being devoid of said pockets;

three support members corresponding to said three pockets of said stiffened section and being removably received therein; and, a plurality of pairs of handle members affixed to said pliant body member, a respective pair of said plurality of pairs of handle members being affixed to each said head supporting portion, torso supporting portion and said leg supporting portion.

2. The portable stretcher system as recited in claim 1 further comprising a carrying case having a tubular wall extending between an open upper end and an opposing closed bottom end to define an open cavity adapted to receive said pliant body member therein subsequent to said pliant body member being folded with said head supporting portion and said leg supporting portion overlying said torso supporting portion and said pliant body member being rolled laterally, said torso supporting portion having said three support members disposed within said pockets.

3. The portable stretcher system as recited in claim 1 where said leg supporting portion has a longitudinal dimension less than a longitudinal dimension of said torso supporting portion.

4. The portable stretcher system as recited in claim 1 where said stiffened section extends laterally a dimension within the approximating range of 12 to 16 inches.

* * * * *